(12) United States Patent
Lu et al.

(10) Patent No.: US 11,051,765 B2
(45) Date of Patent: Jul. 6, 2021

(54) HEALTH STATUS DETECTING SYSTEM AND METHOD FOR DETECTING HEALTH STATUS

(71) Applicant: SHANGHAI OXI TECHNOLOGY CO., LTD, Shanghai (CN)

(72) Inventors: Ketao Lu, Shanghai (CN); Hong Zhu, Shanghai (CN); Weiping Lin, Shanghai (CN)

(73) Assignee: SHANGHAI OXI TECHNOLOGY CO., LTD, Shanghai (CN)

( * ) Notice: Subject to any disclaimer, the term of this patent is extended or adjusted under 35 U.S.C. 154(b) by 158 days.

(21) Appl. No.: 16/066,152

(22) PCT Filed: Dec. 31, 2015

(86) PCT No.: PCT/CN2015/100239
§ 371 (c)(1),
(2) Date: Jun. 26, 2018

(87) PCT Pub. No.: WO2017/113347
PCT Pub. Date: Jul. 6, 2017

(65) Prior Publication Data
US 2019/0008464 A1    Jan. 10, 2019

(51) Int. Cl.
*A61B 5/00* (2006.01)
*A61B 5/02* (2006.01)
(Continued)

(52) U.S. Cl.
CPC .............. *A61B 5/7278* (2013.01); *A61B 5/02* (2013.01); *A61B 5/0205* (2013.01);
(Continued)

(58) Field of Classification Search
CPC ....... A61B 5/7278; A61B 5/02; A61B 5/0205; A61B 5/0245; A61B 5/746; A61B 5/0077;
(Continued)

(56) References Cited

U.S. PATENT DOCUMENTS

2002/0052554 A1    5/2002  Yokozeki
2014/0031646 A1*   1/2014  Yakirevich ........... A61B 5/0464
                                                      600/310
(Continued)

FOREIGN PATENT DOCUMENTS

CN    102058400 A    5/2011
CN    104158914 A   11/2014
(Continued)

OTHER PUBLICATIONS

International Search Report and Written Opinion from PCT/CN2015/100239 dated Nov. 27, 2016.

*Primary Examiner* — Catherine M Voorhees
*Assistant Examiner* — Roland Dinga
(74) *Attorney, Agent, or Firm* — Adsero IP

(57) ABSTRACT

A health status detecting system includes a first acquisition device configured to collect a plurality of images of a finger of a user; a second acquisition device configured to obtain an electrocardiogram of the user; and a processor configured to process the plurality of images to obtain a pulse wave of the user and configured to obtain a blood pressure of the user based on the pulse wave and the electrocardiogram of the user.

19 Claims, 7 Drawing Sheets

(51) Int. Cl.
*A61B 5/0245* (2006.01)
*A61B 5/0205* (2006.01)
*G06K 9/00* (2006.01)
*A61B 5/024* (2006.01)
*A61B 5/318* (2021.01)
*A61B 5/021* (2006.01)
*A61B 5/1172* (2016.01)

(52) U.S. Cl.
CPC ............ *A61B 5/0245* (2013.01); *A61B 5/746* (2013.01); *G06K 9/00013* (2013.01); *G06K 9/00087* (2013.01); *A61B 5/0077* (2013.01); *A61B 5/02125* (2013.01); *A61B 5/02416* (2013.01); *A61B 5/02438* (2013.01); *A61B 5/1172* (2013.01); *A61B 5/318* (2021.01); *A61B 5/6826* (2013.01)

(58) Field of Classification Search
CPC ............ A61B 5/02125; A61B 5/02416; A61B 5/02438; A61B 5/0402; A61B 5/1172; A61B 5/6826; G06K 9/00013; G06K 9/00087
See application file for complete search history.

(56) References Cited

U.S. PATENT DOCUMENTS

| | | | |
|---|---|---|---|
| 2014/0073969 A1* | 3/2014 | Zou | A61B 5/0205 600/479 |
| 2015/0324570 A1* | 11/2015 | Lee | G06K 9/00087 382/124 |

FOREIGN PATENT DOCUMENTS

| | | | |
|---|---|---|---|
| CN | 104523252 A | 4/2015 | |
| CN | 104640498 A | 5/2015 | |
| CN | 104834946 A | 8/2015 | |

* cited by examiner

HEALTH STATUS DETECTING SYSTEM AND METHOD FOR DETECTING HEALTH STATUS

CROSS-REFERENCE TO RELATED APPLICATIONS

This application is the national phase of International Application No. PCT/CN2015/100239, filed on Dec. 31, 2015, and entitled "HEALTH STATUS DETECTING SYSTEM AND METHOD FOR DETECTING HEALTH STATUS".

TECHNICAL FIELD

The present disclosure generally relates to electro-biometric fields, and more particularly, to a health status detecting system and a method for detecting health status.

BACKGROUND

Blood pressure is an important index in indicating a person's health status. It can be obtained using various methods, such as by sphygmomanometer, by pressure sensor, by auscultatory method and by oscillometric method, etc.

However, blood pressure of a person cannot be obtained conveniently according to the need, especially when the person is not at home or at the hospital. Therefore, there is a need for a health status detecting system which can be used timely.

SUMMARY

According to embodiments of the present disclosure, a health status detecting system is provided. The health status detecting system includes: a first acquisition device configured to collect a plurality of images of a finger of a user; a second acquisition device configured to obtain an electrocardiogram (ECG) of the user; and a processor configured to process the plurality of images to obtain a pulse wave of the user and configured to obtain a blood pressure of the user based on the pulse wave and the electrocardiogram of the user.

In some embodiments, the first acquisition device is configured to collect the plurality of images at a speed of tens of frames per second.

In some embodiments, the pulse wave of the user is obtained through detecting a gray value variation among the plurality of images.

In some embodiments, the processor is further configured to obtain a transmission duration of the pulse wave based on the electrocardiogram and pulse wave of the user, and further configured to obtain a transmission speed of the pulse wave based on the transmission duration and a transmission distance.

In some embodiments, the processor is further configured to obtain a corresponding relationship between blood pressures and transmission speeds of the pulse wave.

In some embodiments, the processor is configured to obtain a blood pressure of the user based on the corresponding relationship and the transmission speed of the pulse wave obtained by the system.

In some embodiments, the processor is further configured to compare the blood pressure with the previous blood pressure results of the user, and alert the user if the blood pressure obtained this time deviates from the previous blood pressure results greater than a threshold.

In some embodiments, the processor is further configured to process several of the plurality of images to obtain a fingerprint of the user.

In some embodiments, the processor is further configured to determine whether the fingerprint of the user matches one of the user's fingerprints pre-stored in the system.

In some embodiments, the processor is further configured to process the pulse wave to obtain a characteristic pulse information of the user, or to process the electrocardiogram to obtain a characteristic ECG information of the user; and the processor is further configured to determine whether the pulse wave or ECG belongs to a live human based on the characteristic pulse information of the user or the characteristic ECG information of the user, respectively.

In some embodiments, the system further includes a display device configured to display the blood pressure, electrocardiogram, pulse wave or alert to the user.

In some embodiments, the health status detecting system is integrated in a mobile terminal device.

In some embodiments, the second acquisition device obtains an electrocardiogram through measuring a voltage difference or a current difference or a charge difference between two hands of the user.

In some embodiments, the second acquisition device shares a common electrode with the first acquisition device.

In addition, embodiments of the present disclosure further provide a method for detecting a health status, includes: collecting a plurality of images of a finger of a user; obtaining an electrocardiogram of the user; processing the plurality of images to obtain a pulse wave of the user; and obtaining a blood pressure of the user based on the pulse wave and the electrocardiogram.

In some embodiments, the plurality of images is collected at a speed of tens of frames per second.

In some embodiments, the pulse wave of the user is obtained through processing the plurality of images to obtain a gray value variation among the plurality of images.

In some embodiments, obtaining a blood pressure of the user based on the pulse wave and electrocardiogram includes: obtaining a transmission duration of the pulse wave based on the electrocardiogram and the pulse wave of the user; obtaining a transmission speed of the pulse based on the transmission duration and a transmission distance; obtaining a corresponding relationship between blood pressures and transmission speeds of the pulse wave; and obtaining a blood pressure of the user based on the corresponding relationship and the transmission speed of the pulse wave obtained by the system.

In some embodiments, the method further includes: comparing the blood pressure with the previous blood pressure results of the user; and alerting the user if the blood pressure obtained this time deviates from the previous blood pressure results greater than a threshold.

In some embodiments, the method further includes: processing several of the plurality of images to obtain a fingerprint of the user.

In some embodiments, the method further includes: determining whether the fingerprint of the user matches one of the user's fingerprints pre-stored in the system.

In some embodiments, the method further includes: processing the pulse wave to obtain a characteristic pulse information of the user, or to process the electrocardiogram to obtain a characteristic ECG information of the user; and determining whether the pulse wave or ECG belongs to a live human based on the characteristic pulse information of the user or the characteristic ECG information of the user, respectively.

In some embodiments, the method further includes: displaying the blood pressure, electrocardiogram, pulse wave or alert to the user.

In some embodiments, the electrocardiogram is obtained through measuring a voltage difference, or a current difference, or a charge difference between two hands of the user.

By obtaining the blood pressure based on the pulse wave and the electrocardiogram, the health status detecting system can share some of its parts with a mobile terminal device and thus the health status detecting system can be integrated in a mobile terminal device, which makes it convenient to use, especially when the user is not at home or at the hospital.

The health status detecting system provided in the embodiments can alert the user if the blood pressure deviates from the previous blood pressure results greater than a threshold, which makes it possible for the user to know about his health status at an earliest time.

DETAILED DESCRIPTION

In order to clarify the objects, characteristics and advantages of the present disclosure, embodiments of the present disclosure will be described in detail in conjunction with the accompanying drawings. The disclosure will be described with reference to certain embodiments. Accordingly, the present disclosure is not limited to the embodiments disclosed. It will be understood by those skilled in the art that various changes may be made without departing from the spirit or scope of the disclosure.

Figure 1:
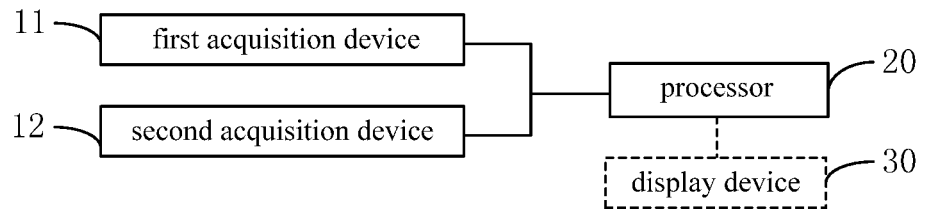
FIG. 1 schematically illustrates a function block diagram of a health status detecting system.

Referring to FIG. 1, a function block diagram of a health status detecting system is schematically illustrated. The health status detecting system includes: a first acquisition device 11, a second acquisition device 12, a processor 20 and a display device 30.

The first acquisition device 11 is configured to collect a plurality of images of a finger of a user. In some embodiments, the first acquisition device 11 may be configured to collect the plurality of images at a speed of tens of frames per second. In some embodiments, the speed is sixty-five frames per second. The first acquisition device 11 may also be provided with a touch window for placing a finger.

In some embodiments, the first acquisition device 11 may use a fingerprint identification sensor to realize the above function. For example, an optical fingerprint identification sensor can be used as the first acquisition device 11. In some other embodiments, a capacitance, a thermosensitive, or a pressure-sensitive type fingerprint identification sensor can also be used as the first acquisition device 11.

Figure 2:
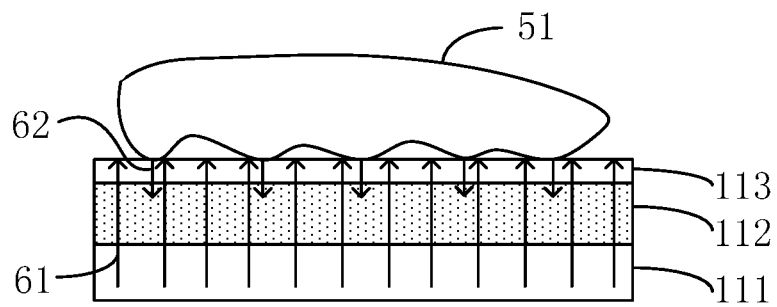
FIG. 2 schematically illustrates a principle of collecting a plurality of images of a finger of a user by a first acquisition device.

FIG. 2 schematically illustrates a principle of collecting a plurality of images of a finger of a user by a first acquisition device 11 shown in FIG. 1. Specifically, FIG. 2 shows an optical fingerprint identification sensor for exemplary purpose. The optical fingerprint identification sensor includes a backlight plate 111, an optical array sensor 112 and a protective glass 113. Referring to FIG. 2, the principle for collecting one finger image by the first acquisition 11 is as follows: the user puts one of his finger 51 on the protective glass 113; the backlight plate 111 provides an incident light 61 to illuminate the finger 51; the incident light 61 goes through the optical array sensor 112 and the protective glass 113, and then is reflected and transmitted on the interface between the finger 51 and protective glass 113, resulting in a reflected light 62; the reflected light 62 goes through the protective glass 113 and irradiates on the optical array sensor 112; the optical array sensor 112 conducts a photoelectric conversion and signal processing, thus realizing to collect an image of a finger of the user. Then the first acquisition device 11 repeatedly collects the image of the finger of the user at a certain speed in order to obtain a plurality of images of the finger of the user.

The second acquisition device 12 is configured to obtain an electrocardiogram of the user. In some embodiments, the second acquisition device 12 is configured to obtain an electrocardiogram through measuring a voltage variation between the two hands of the user placed on two electrodes. The second acquisition device 12 may be a voltage sensor including at least two electrodes. The voltage variation between the two hands may be obtained by detecting voltages on two fingers placed on two electrodes of the voltage sensor. As described above, the first acquisition device 11 may be a fingerprint identification sensor; the fingerprint identification sensor includes a touch window for placing a finger. In some embodiments, the touch window can also act as an electrode to detect voltage signal of a finger. Alternatively, in some embodiments, the iron hoop outside the fingerprint identification sensor can act as an electrode to detect voltage signal of a finger as well. In this way, the second acquisition device 12 may use the touch window or the iron hoop of the first acquisition device 11 as an electrode to reduce the area of the health status detecting system, that is, the second acquisition device 12 may share a common electrode with the first acquisition device 11.

In some embodiments, the electrocardiogram may also be obtained through detecting current difference or charge difference between two hands. The principle for the detection is similar to the voltage sensor. In some embodiments, the voltage variation signal can also be collected between arms or wrists, and the electrocardiogram may also be obtained using any kind of the current standard 12-lead ways.

Figure 3:
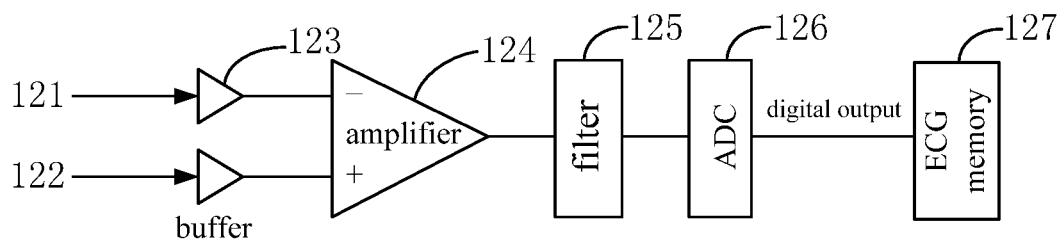
FIG. 3 schematically illustrates a processing circuit of a second acquisition device according to an embodiment of the present disclosure.

FIG. 3 schematically illustrates a processing circuit of the second acquisition device 12 according to an embodiment of the present disclosure. The processing circuit includes an electrode 121 and an electrode 122 for acquiring a voltage variation signal from the user's body; a buffer 123 for impedance matching; an amplifier 124 for amplifying the voltage variation signal; a filter 125 for filtering the noise in the amplified voltage variation signal; an analog to digital converter (ADC) 126 for transforming the analog voltage variation signal into an electrocardiogram signal; after ADC, the voltage variation signal is transformed into an electrocardiogram and stored in an ECG memory 127.

Figure 4:
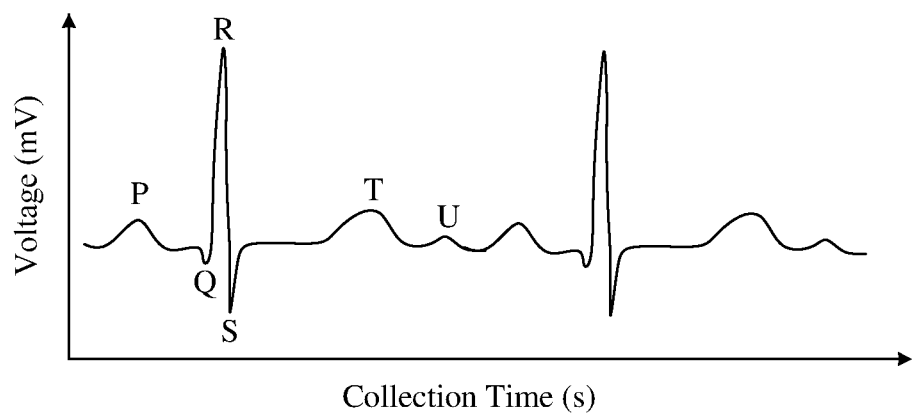
FIG. 4 schematically illustrates an electrocardiogram obtained by the second acquisition device according to an embodiment of the present disclosure.

As shown in FIG. 4, an electrocardiogram obtained by the second acquisition device 12 is schematically illustrates. A complete electrocardiogram consists of a P wave, QRS wave, T wave and U wave, which reflect the different phase of the cardiac activity. The above information is a characteristic ECG information, which can be used for determining whether the electrocardiogram belonging to a live human.

The processor 20 is configured to process the plurality of images to obtain a pulse wave of the user. In some embodiments, the pulse wave of the user may be obtained through detecting a gray value variation among the plurality of images. Referring to FIG. 2, in principle, the reflection and absorption of the incident light 61 is influenced by the blood flow in the finger 51, the intensity of the reflected light 62 irradiating on the optical array sensor 112 changes with the blood flow. Therefore, the gray value of an image of the finger 51 will be influenced by the blood flow. Accordingly, a gray value variation of the successively collected plurality of images of a finger of a user reflect the variation of the user's pulse, that is, the pulse wave.

In practice, the method for the processor 20 obtaining a pulse wave of the user is as follows: the processor 20 obtains a gray value for each of the plurality of images of the finger of the user; thereafter, according to the collection sequence of the plurality of images, the processor 20 obtains a relationship between the gray value and time to form the pulse wave. It should be noted, a filtering process may be performed to the pulse wave to filter a noise in the pulse wave to improve the accuracy of the pulse wave. The noise may include an external interference like ambient light, and an internal interference like circuit noise. All these interferences have a negative influence on the pulse wave and should be eliminated. Arithmetic average filtering or recurrence average filtering method etc. may be adopted to filter the noise.

It should be noted that, in some embodiments, the average gray value in a central region of each of the plurality of images with a pixel area 90×90 is selected as a representative gray value for each of the plurality of images.

Figure 5:
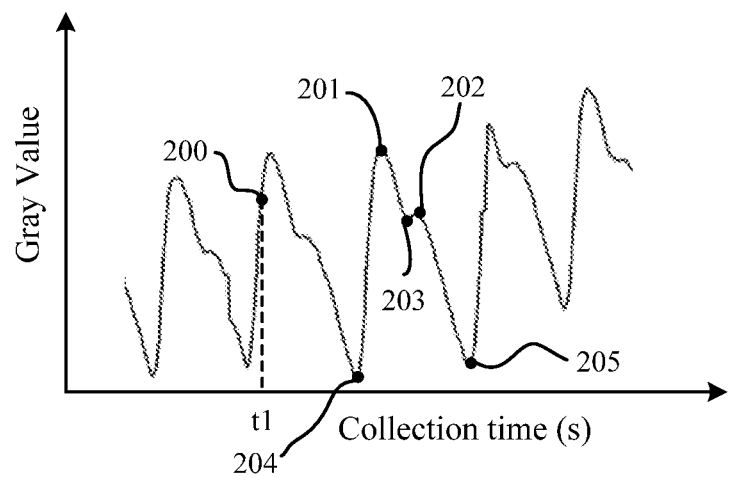
FIG. 5 schematically illustrates a pulse wave acquired by a processor according to an embodiment of the present disclosure.

FIG. 5 schematically illustrates a pulse wave acquired by the processor 20 according to an embodiment of the present disclosure. As shown in FIG. 5, the horizontal axis is corresponding to a collection time for each of the plurality of images, and the vertical axis is corresponding to the gray value for each of the plurality of images. For example, the data point 200 represents the gray value of the finger image collected by the first acquisition device 11 at the moment of t1. The gray values at different collection time, namely a gray value variation, forms a pulse wave curve. In some embodiments, a characteristic pulse information includes five data points at least: the two peaks points 201 and 202, the valley point 203, the start point 204 and the end point 205, which can be used for determining whether the pulse wave belongs to a live human.

Figure 6:
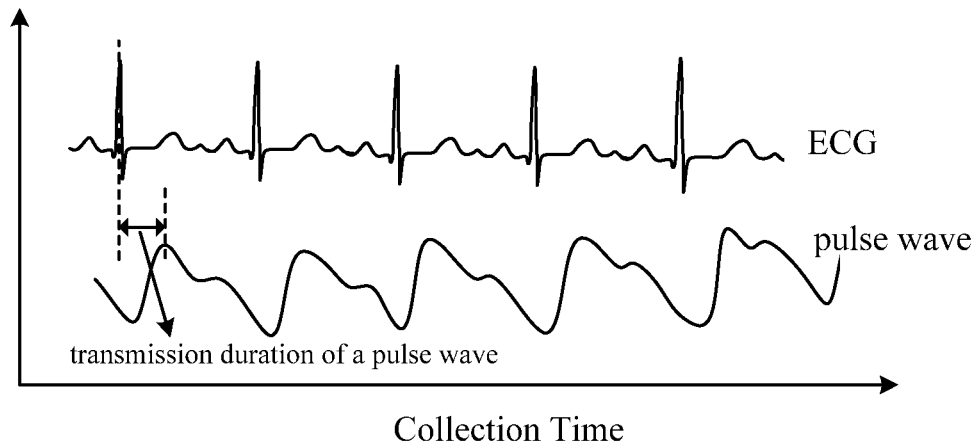
FIG. 6 schematically illustrates a method for obtaining a transmission duration of the pulse wave based on the electrocardiogram and the pulse wave of the user.

The processor 20 is further configured to obtain a transmission duration of the pulse wave based on the electrocardiogram and the pulse wave of the user. FIG. 6 schematically illustrates a method for obtaining a transmission duration based on the electrocardiogram and the pulse wave of the user. The transmission duration can be obtained by calculating a time period between the peak on the ECG and the peak on the pulse wave. A transmission distance for the pulse wave is from the heart to the finger of the user. Therefore, the transmission speed of the pulse wave can be obtained by the processor 20 by dividing the transmission distance by the transmission duration.

Figure 7:
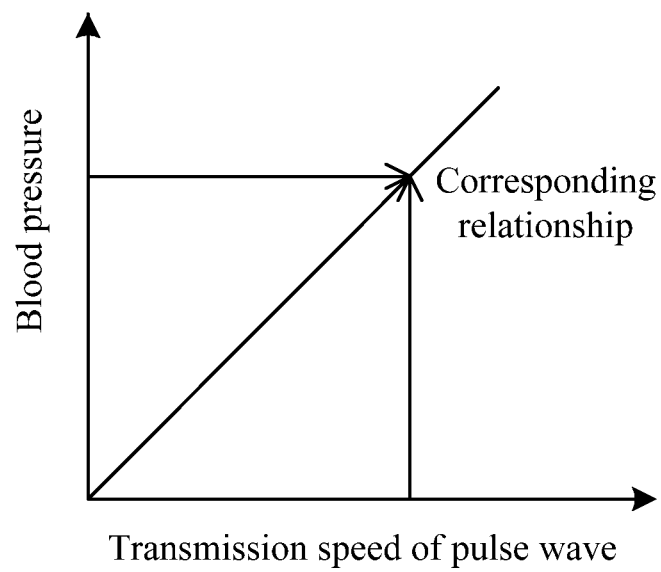
FIG. 7 schematically illustrates a corresponding relationship between blood pressures and transmission speeds of the pulse wave according to an embodiment of the present disclosure.
Figure 8:
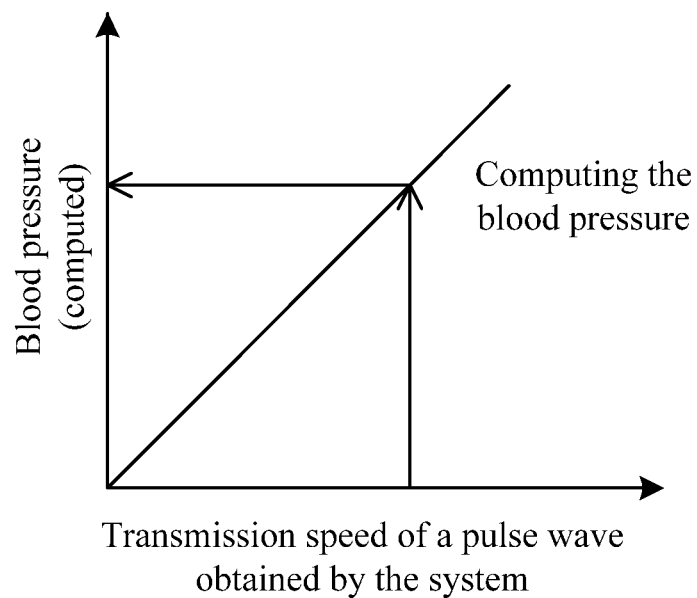
FIG. 8 schematically illustrates a method for obtaining a blood pressure based on the corresponding relationship shown in FIG. 7 and a transmission speed of the pulse wave obtained by the system.

Further, the processor 20 is also configured to invoke a relationship between blood pressures and transmission speeds of the pulse wave. FIG. 7 schematically illustrates a corresponding relationship between blood pressures and transmission speeds of the pulse wave according to an embodiment of the present disclosure. As is shown in FIG. 7, the blood pressure is a linear function of the transmission speed of pulse wave. As long as either the transmission speed of the pulse wave or the blood pressure is known, the other one can be obtained. FIG. 8 schematically illustrates a method for obtaining a blood pressure based on the corresponding relationship shown in FIG. 7 and the transmission speed of the pulse wave obtained by the system. The processor 20 obtains a blood pressure corresponding to the transmission speed of the pulse wave obtained by the system based on the relationship.

In some embodiments, the health status detecting system further includes a memory for storing the blood pressure of the user. With this, the processor is further configured to compare the blood pressure to previous blood pressure results of the user, and to alert the user if the blood pressure obtained this time deviates from the previous blood pressure results greater than a threshold. In some embodiments, the threshold may be 60 mmHg. The alert may be a brief word displayed on the display device, such as: Your blood pressure is abnormal. The user may decide to see a doctor for the abnormal, which makes it possible for the user to know about his health status at an earliest time.

In some embodiments, the health status detecting system further includes a display device 30 (as shown in FIG. 1) configured to display the results to the user. The results may include the blood pressure, electrocardiogram, pulse wave or alert.

As described above, the first acquisition device 11 can employ an optical fingerprint identification sensor. Therefore, the health status detecting system can also be used as a fingerprint identification device. Specifically, the processor 20 is also configured to process several of the plurality of images to obtain a fingerprint of the user. In some embodiments, the processor 20 is configured to process four of the plurality of images and do some arithmetic to obtain the fingerprint of the user. Then the processor 20 determines whether the fingerprint of the user matches one of the user's fingerprints pre-stored in the system. If yes, then the identification of the user is passed.

In some embodiments, the fingerprint identification process can be performed before the blood pressure obtaining process. The fingerprint identification process or the blood pressure obtaining process is more meaningful when the fingerprint belongs to a live human. Therefore, a process of determining whether the user is a live human is necessary. In some embodiments, before the fingerprint identification process, the health status detecting system is configured to determine whether the user is a live human from the characteristic pulse information or the characteristic ECG information. Specifically, the processor 20 is configured to process the pulse wave of the user to obtain the characteristic pulse information, or to process the electrocardiogram to obtain the characteristic ECG information. Thereafter, by virtue of the characteristic pulse information or the characteristic ECG information of the user, the processor 20 can determine whether the pulse wave or ECG belongs to a live human. In some embodiments, the characteristic pulse information may includes the characteristic points of the pulse wave as shown in FIG. 5, as well as the frequency of the pulse wave; the characteristic information of the electrocardiogram may include the information reflected by the P wave, QRS wave, T wave and U wave as shown in FIG. 4.

Figure 9:
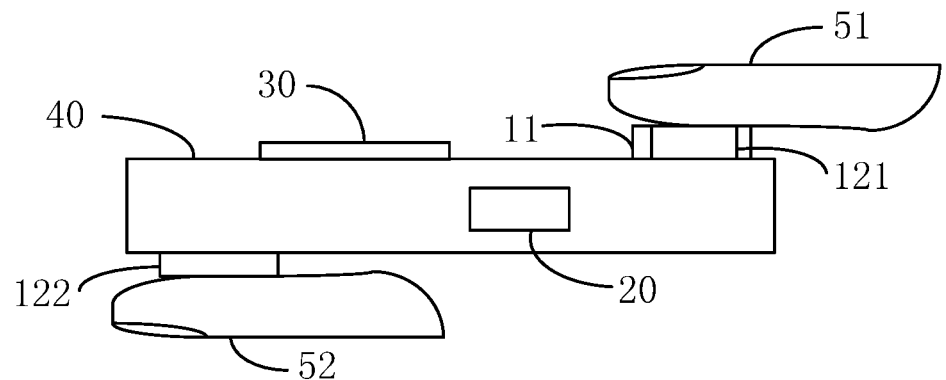
FIG. 9 schematically illustrates a diagram of using a health status detecting system according to an embodiment of the present disclosure.

The health status detecting system can be integrated in a mobile terminal device. FIG. 9 schematically illustrates a diagram of using a health status detecting system according to an embodiment of the present disclosure. Referring to FIG. 1 and FIG. 9, the first acquisition device 11 and the second acquisition device 12 are configured on the shell of a mobile terminal device 40. The second acquisition device 12 includes two electrodes 121 and 122 configured on the two sides of the mobile terminal device 40, for detecting the voltage variation between two fingers 51 and 52 in the user's two hands. The second acquisition device 12 shares a common electrode 121 with the first acquisition device 11. The processor 20 is integrated in the inside of the mobile terminal device 40. A displayer 30 of the mobile terminal device 40 can be used to display the blood pressure, electrocardiogram, pulse wave or alert to the user.

By employing an identification function, including the fingerprint identification and live human identification in a health status detecting system, the health status detecting system is multi-functional and highly-integrated. A user doesn't need to carry several devices with him at the same time.

Figure 10:
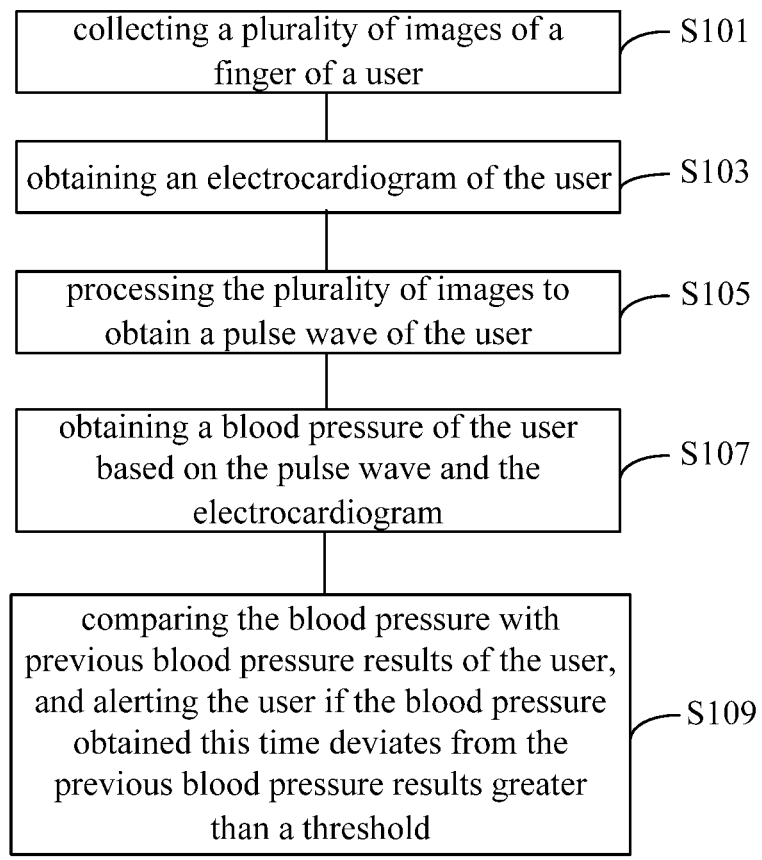
FIG. 10 schematically illustrates a flow chart of a method for obtaining the blood pressure according to an embodiment of the present disclosure.

A method for detecting health status is also provided. Referring to FIG. 10, a flow chart of a method for detecting health status is schematically illustrates.

In S101, a first acquisition device collects a plurality of images of a finger of a user.

In S103, a second acquisition device obtains an electrocardiogram of the user.

In S105, a processor processes the plurality of images to obtain a pulse wave of the user.

In S107, the processor obtains a blood pressure of the user based on the pulse wave and the electrocardiogram.

In S109, the processor compares the blood pressure with the previous blood pressure results of the user, and alerts the user if the blood pressure obtained this time deviates from the previous blood pressure results greater than a threshold.

Figure 11:
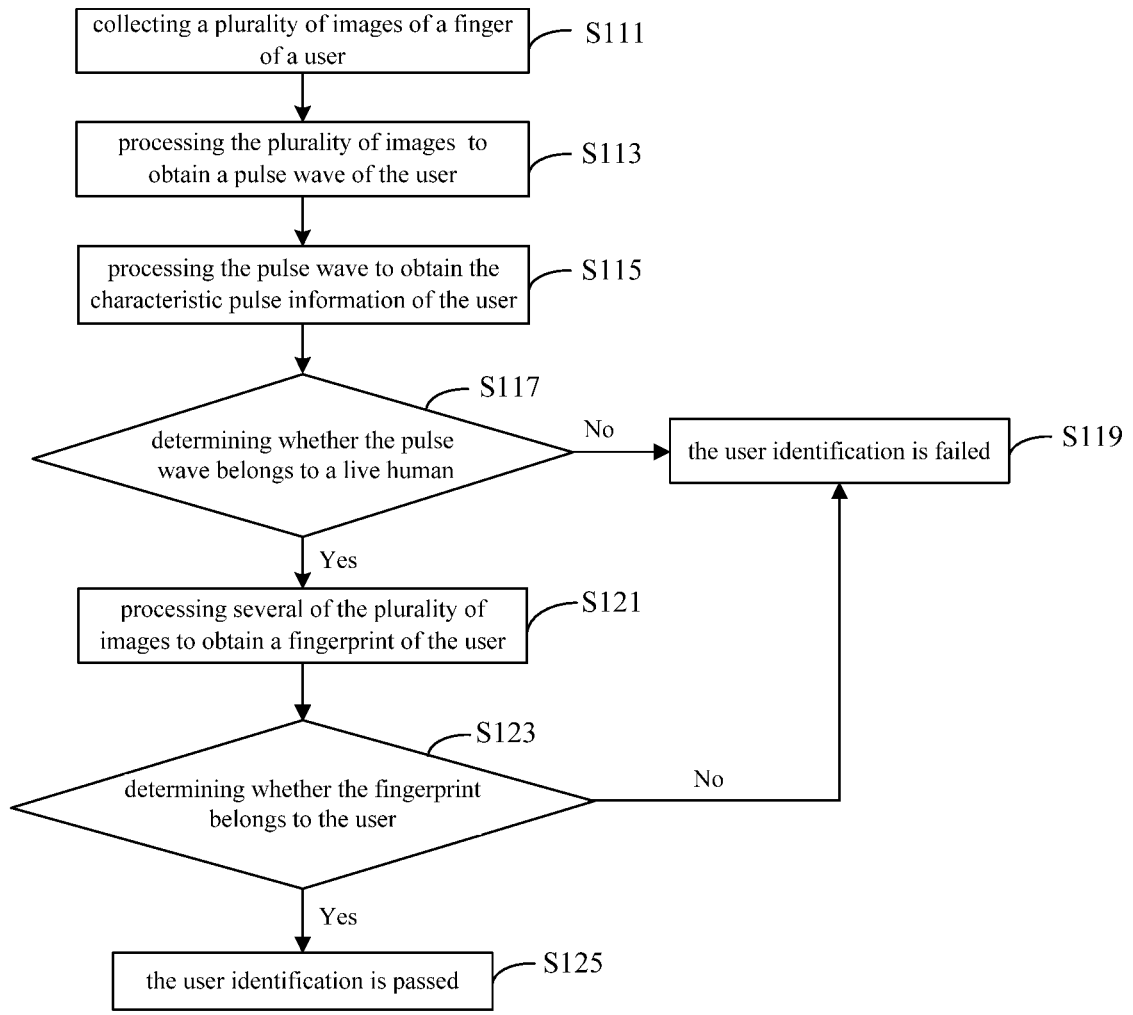
FIG. 11 schematically illustrates a flow chart of a method for a user identification according to an embodiment of the present disclosure.

Another method for detecting a health status is provided. In some embodiment, a user identification process is conducted prior to detecting a health status of the user. Referring to FIG. 11, a flow chart of a method for a user identification is schematically illustrates.

In S111, a first acquisition device collects a plurality of images of a finger of a user.

In S113, a processor processes the plurality of images to obtain a pulse wave of the user.

In S115, the processor processes the pulse wave to obtain the characteristic pulse information of the user.

In S117, the processor determines whether the pulse wave belongs to a live human. If yes, the method is directed to S121. Otherwise, the method is directed to S119, that is, the user identification is failed.

In S121, the processor processes several of the plurality of images to obtain a fingerprint of the user.

In S123, the processor determines whether the fingerprint belongs to the user. Specifically, the processor determines whether the fingerprint matches one of the user's fingerprints pre-stored in the system. If yes, the method is directed to S125. Otherwise, the method is directed to S119, that is, the user identification is failed.

In S125, the user identification is passed.

Thereafter, if the user identification is passed, the method is directed to the process for detecting health status of the user as shown in S103, S107 and S109 in FIG. 10.

Figure 12:
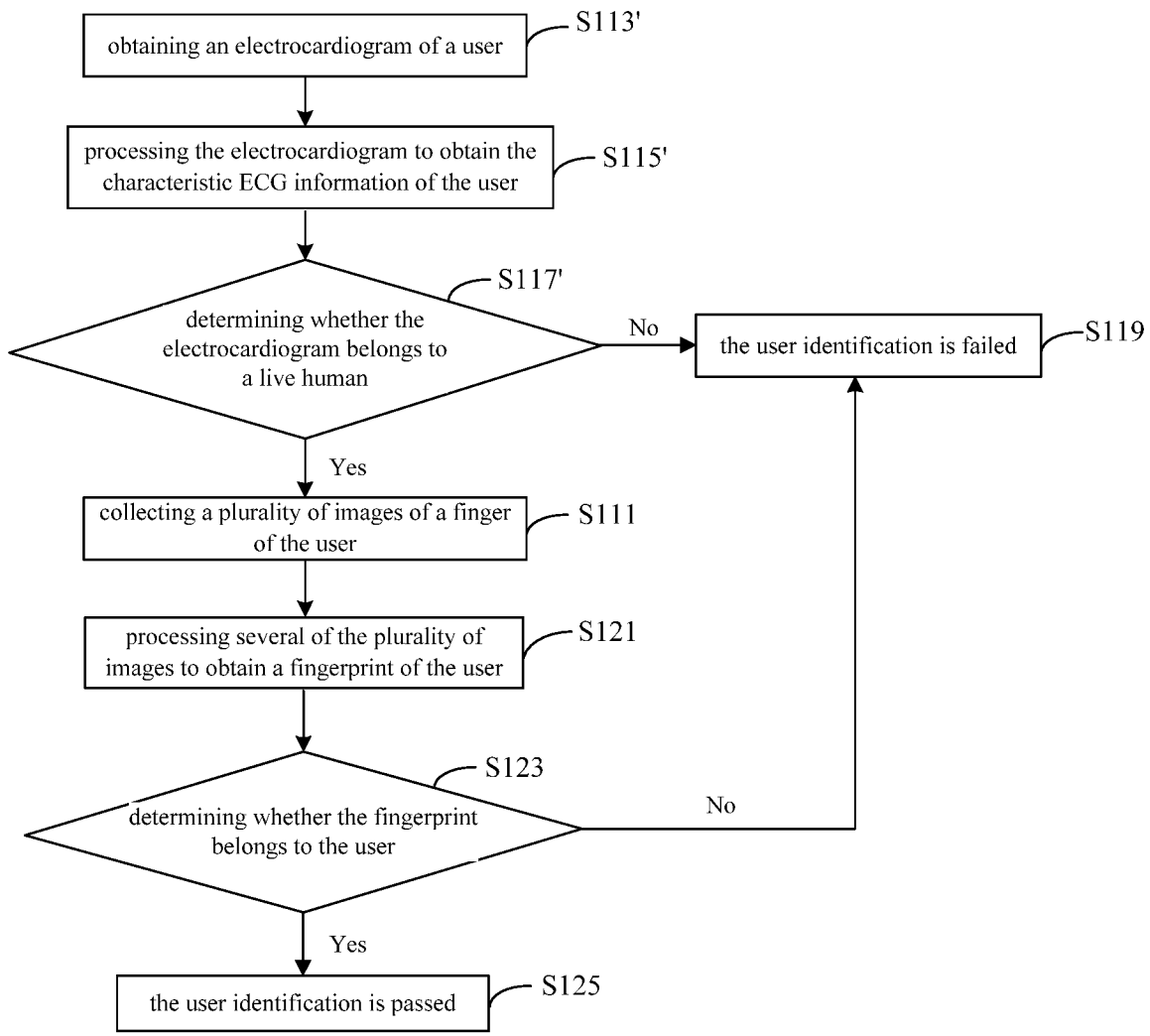
FIG. 12 schematically illustrates a flow chart of a method for a user identification according to an embodiment of the present disclosure.

In some embodiments, the user identification can be conducted using another method. Referring to FIG. 12, a flow chart of a method for a user identification is provided.

In S113', a second acquisition device obtains an electrocardiogram of a user.

In S115', a processor processes the electrocardiogram to obtain the characteristic electrocardiogram information of the user.

In S117', the processor determines whether the electrocardiogram belongs to a live human. If yes, the method is directed to S111. Otherwise, the method is directed to S119, that is, the user identification is failed.

In S111, a first acquisition device collects a plurality of images of a finger of the user.

In S121, the processor processes several of the plurality of images to obtain a fingerprint of the user.

In S123, the processor determines whether the fingerprint belongs to the user. Specifically, the processor determines whether the fingerprint matches one of the user's fingerprints pre-stored in the system. If yes, the method is directed to S125. Otherwise, the method is directed to S119, that is, the user identification is failed.

In S125, the user identification is passed.

Thereafter, if the user identification is passed, the method is directed to the process for detecting health status of the user as shown in S105, S107 and S109 in FIG. 10.

The above described and other features and advantages will become more apparent to those of ordinary skill in the art by describing in detail exemplary embodiments with reference to the attached drawings. The same reference numbers may be used in different drawings to identify the same or similar elements. The figures are not drawn to scale, and the emphasis is to illustrate the disclosure instead.

What is claimed is:

1. A health status detecting system, comprising:
a first acquisition device configured to collect a plurality of images of a finger of a user;
a second acquisition device configured to obtain an electrocardiogram of the user;
a processor configured to process the plurality of images to obtain a pulse wave of the user and configured to obtain a blood pressure of the user based on the pulse wave and the electrocardiogram of the user,
wherein the processor is further configured to obtain a transmission duration of the pulse wave based on the electrocardiogram and pulse wave of the user, and further configured to obtain a transmission speed of the pulse wave based on the transmission duration and a transmission distance.

2. The system according to claim 1, wherein the first acquisition device is configured to collect the plurality of images at a speed of tens of frames per second.

3. The system according to claim 1, wherein the pulse wave of the user is obtained through detecting a gray value variation among the plurality of images.

4. The system according to claim 1, wherein the processor is further configured to obtain a corresponding relationship between blood pressures and transmission speeds of pulse wave.

5. The system according to claim 4, wherein the processor is configured to obtain the blood pressure of the user based on the corresponding relationship and the transmission speed of the pulse wave obtained by the system.

6. The system according to claim 1, wherein the processor is further configured to compare the blood pressure with previous blood pressure results of the user, and alert the user if the blood pressure obtained this time deviates from the previous blood pressure results greater than a threshold.

7. The system according to claim 1, wherein the second acquisition device obtains an electrocardiogram through measuring a voltage difference or a current difference or a charge difference between two hands of the user.

8. The system according to claim 1, wherein the second acquisition device shares a common electrode with the first acquisition device.

9. The system according to claim 1, wherein the processor is further configured to process several of the plurality of images to obtain a fingerprint of the user.

10. The system according to claim 9, wherein the processor is further configured to determine whether the fingerprint of the user matches one of the user's fingerprints pre-stored in the system.

11. The system according to claim 10, wherein the processor is further configured to process the pulse wave to obtain a characteristic pulse information of the user, or to process the electrocardiogram to obtain a characteristic electrocardiogram information of the user; and the processor is further configured to determine whether the pulse wave or electrocardiogram belongs to a live human based on the characteristic pulse information of the user or the characteristic electrocardiogram information of the user, respectively.

12. A method for detecting health status, comprising:
collecting a plurality of images of a finger of a user;
obtaining an electrocardiogram of the user;
processing the plurality of images to obtain a pulse wave of the user;
obtaining a blood pressure of the user based on the pulse wave and the electrocardiogram,
wherein obtaining the blood pressure of the user based on the pulse wave and electrocardiogram comprises:
obtaining a transmission duration of the pulse wave based on the electrocardiogram and the pulse wave of the user; and
obtaining a transmission speed of the pulse wave based on the transmission duration and a transmission distance.

13. The method according to claim 12, wherein the pulse wave of the user is obtained through processing the plurality of images to get a gray value variation among the plurality of images.

14. The method according to claim 12, wherein obtaining the blood pressure of the user based on the pulse wave and electrocardiogram further comprises:
obtaining a corresponding relationship between blood pressures and transmission speeds of pulse wave; and
obtaining the blood pressure of the user based on the corresponding relationship and the transmission speed of the pulse wave obtained by the system.

15. The method according to claim 12, further comprising:
comparing the blood pressure with the previous blood pressure results of the user; and
alerting the user if the blood pressure obtained this time deviates from the previous blood pressure results greater than a threshold.

16. The method according to claim 12, further comprising:
processing the pulse wave to obtain a characteristic pulse information of the user, or to process the electrocardiogram to obtain a characteristic electrocardiogram information of the user; and determining whether the pulse wave or electrocardiogram belongs to a live human based on the characteristic pulse information of the user or the characteristic electrocardiogram information of the user, respectively.

17. The method according to claim 12, wherein the electrocardiogram is obtained through measuring a voltage difference, or a current difference, or a charge difference between two hands of the user.

18. The method according to claim 12, wherein the method further comprises:
processing several of the plurality of images to obtain a fingerprint of the user.

19. The method according to claim 18, further comprising: determining whether the fingerprint of the user matches one of the user's fingerprints pre-stored in the system.

* * * * *